(12) United States Patent
Itoh et al.

(10) Patent No.: US 10,478,156 B2
(45) Date of Patent: Nov. 19, 2019

(54) IMAGING APPARATUS FOR DIAGNOSIS, METHOD OF CONTROLLING THE SAME, PROGRAM, AND COMPUTER READABLE STORAGE MEDIUM

(71) Applicant: TERUMO KABUSHIKI KAISHA, Shibuya-ku, Tokyo (JP)

(72) Inventors: Ema Itoh, Kanagawa (JP); Isao Mori, Kanagawa (JP)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 891 days.

(21) Appl. No.: 15/081,371

(22) Filed: Mar. 25, 2016

(65) Prior Publication Data
US 2016/0206290 A1    Jul. 21, 2016

Related U.S. Application Data

(63) Continuation of application No. PCT/JP2014/004848, filed on Sep. 22, 2014.

(30) Foreign Application Priority Data

Sep. 27, 2013 (JP) ................................ 2013-201406

(51) Int. Cl.
*A61B 5/00* (2006.01)
*A61B 8/08* (2006.01)
(Continued)

(52) U.S. Cl.
CPC .......... *A61B 8/5223* (2013.01); *A61B 5/0066* (2013.01); *A61B 5/0073* (2013.01);
(Continued)

(58) Field of Classification Search
CPC ... A61B 5/0084; A61B 5/7257; A61B 5/6852; A61B 5/0073; A61B 5/02007;
(Continued)

(56) References Cited

FOREIGN PATENT DOCUMENTS

| JP | 11-056752 A | 3/1999 |
|---|---|---|
| JP | 2006-204430 A | 8/2006 |
| JP | 2011-152274 A | 8/2011 |

OTHER PUBLICATIONS

International Search Report (PCT/ISA/210) dated Jan. 6, 2015, by the Japanese Patent Office as the International Searching Authority for International Application No. PCT/JP2014/004848.
(Continued)

*Primary Examiner* — Joel Lamprecht
(74) *Attorney, Agent, or Firm* — Buchanan Ingersoll & Rooney PC

(57) ABSTRACT

An imaging apparatus, method, and computer readable medium are disclosed, which can detect in a case where a foreign substance such as air and blood other than transparent liquid is present inside a catheter, and can urge a user to perform priming so that an image having higher accuracy can be reconstructed. According to the present disclosure, the imaging apparatus can determined whether or not the foreign substance such as air and blood is present between an imaging core and an inner surface of a catheter sheath, from line data which is generated based on interference light data obtained when the priming is performed or at stages before and after pull-back scanning is performed. In a case where the foreign substance enters, a message urging the user to perform the priming is displayed.

12 Claims, 9 Drawing Sheets

(51) Int. Cl.
*A61B 8/12* (2006.01)
*A61B 8/00* (2006.01)
*A61B 8/14* (2006.01)

(52) U.S. Cl.
CPC .......... *A61B 5/0084* (2013.01); *A61B 5/6852* (2013.01); *A61B 5/6876* (2013.01); *A61B 5/7221* (2013.01); *A61B 8/0891* (2013.01); *A61B 8/12* (2013.01); *A61B 8/445* (2013.01); *A61B 8/4416* (2013.01); *A61B 8/4461* (2013.01); *A61B 8/4494* (2013.01); *A61B 8/461* (2013.01); *A61B 8/5207* (2013.01); *A61B 8/5261* (2013.01); *A61B 8/14* (2013.01); *A61B 8/4281* (2013.01); *A61B 8/463* (2013.01); *A61B 8/54* (2013.01)

(58) Field of Classification Search
CPC ....... A61B 5/742; A61B 1/015; A61B 5/0066; A61B 1/07; A61B 1/00172; A61B 1/00165; A61B 2576/02
See application file for complete search history.

(56) References Cited

OTHER PUBLICATIONS

Written Opinion (PCT/ISA/237) dated Jan. 6, 2015, by the Japanese Patent Office as the International Searching Authority for International Application No. PCT/JP2014/004848.

WHEN BLOOD IS PRESENT
INSIDE CATHETER SHEATH

IMAGING APPARATUS FOR DIAGNOSIS, METHOD OF CONTROLLING THE SAME, PROGRAM, AND COMPUTER READABLE STORAGE MEDIUM

CROSS-REFERENCES TO RELATED APPLICATIONS

This application is a continuation of International Application No. PCT/JP2014/004848 filed on Sep. 23, 2014, which application claims priority to Japanese Patent Application No. 2013-201406, filed on Sep. 27, 2013, the entire contents of which are incorporated herein by reference.

TECHNICAL FIELD

The present disclosure relates to an imaging apparatus for diagnosis, a method of controlling the same, a program, and a computer readable storage medium.

BACKGROUND DISCUSSION

In imaging apparatuses for diagnosis, that is, apparatuses which acquire images of a vascular lumen, there are, for example, an intravascular ultrasound (IVUS) apparatus and an optical coherence tomography (OCT) apparatus.

In the above-described imaging apparatus for diagnosis, an imaging core including a configuration of emitting ultrasound waves or light and a configuration of receiving reflected waves or light from a vascular tissue thereof is contained in a catheter sheath.

The OCT can obtain an image of a vascular lumen surface having high resolution. However, it is only possible to obtain an image from the vascular lumen surface to a relatively shallow tissue. Meanwhile, in a case of the IVUS, even though the resolution of an image, which can be obtained, is lower than that of the OCT, in contrast, an image of a vascular tissue deeper than that of the OCT can be obtained. Recently, an imaging apparatus for diagnosis having the function of the IVUS and the function of the OCT combined together (an imaging apparatus for diagnosis provided with an ultrasound wave transceiver which can transceive ultrasound waves and an optical transceiver which can transceive light) has been proposed (for example, refer to JP-A-11-56752 and JP-A-2006-204430).

Liquid which is a medium of transmitting signals transceived by an imaging core is sometimes contained in a space between the imaging core and a catheter sheath. For example, in a case of a diagnostic apparatus utilizing optical interference, the liquid is contained in the space between the imaging core and the catheter sheath, and thus, it is possible to facilitate the design of an optical member which is generally positioned at a distal end of the imaging core. The reason is that refraction of light can be reduced on an interface of the optical member and an interface of the catheter sheath by containing liquid having a refractive index closer to the refractive index of the optical member or the refractive index of the catheter sheath compared to the refractive index of air.

In addition, ultrasound waves are remarkably attenuated in the air, and when air is present between an ultrasound transducer and a test object, most of the ultrasound waves are totally reflected by the interface therebetween so that the ultrasound waves are not transmitted to the test object. In a case of IVUS, in order to minimize the attenuation or the total reflection of ultrasound waves caused by air so as to be as low as possible, a space between the imaging core and the catheter sheath can be filled with liquid, thereby suppressing degradation of propagation efficiency of ultrasound waves with respect to the test object.

In order to fill the space between the imaging core and the catheter sheath with liquid, air (air bubble) therebetween needs to be easily discharged to the outside. In other words, priming needs to be able to be easily performed. Therefore, generally, a hole for releasing air is provided in the distal end of the catheter sheath (side where the imaging core is present). The reason is that when liquid (generally, a physiological salt solution) is injected from the opposite end, air inside the catheter sheath can be discharged to the outside.

Incidentally, determining whether or not the priming is normally performed is based on the fact that liquid is discharged through the hole in the distal end of the catheter sheath, and the priming is considered to be completed. The reason is that the catheter sheath is an extremely small tube and it can be difficult to visually check the catheter sheath.

Moreover, on the contrary, the hole for releasing air provided in the distal end of the catheter sheath sometimes causes inconvenience. That is the problem of blood flowing into the catheter sheath through pull-back processing which can be performed after the distal end of the catheter sheath is positioned inside a blood vessel which is a diagnostic target. In the pull-back processing, since the imaging core is pulled along a rotary axis thereof while being rotated, the inside of the catheter sheath is under relatively negative pressure with respect to the outside of the catheter sheath. As a result thereof, blood flows into the catheter sheath through the hole in the distal end of the catheter sheath, thereby leading to a problem.

In addition, when a catheter indwells in a blood vessel for a long period of time, blood sometimes flows into the catheter sheath due to the blood pressure inside the blood vessel even though the pull-back processing is not performed. Since blood is an opaque liquid, in a case of the diagnostic apparatus utilizing optical interference, an obtained image is likely to be blurred.

Blood which has flowed into the catheter sheath can be removed by reinjecting liquid such as a saline, which is unlikely to influence a human body, through the proximal end of the catheter sheath similar to the priming. However, in order to realize the removal, there is a need to know that the blurred image is caused by blood flowing into the catheter sheath.

SUMMARY

The present disclosure has been made in consideration of the aforementioned problems. This description provides a technique of detecting that air or blood other than transparent liquid has entered a catheter sheath and notifying a user thereof in the imaging apparatus for diagnosis.

An imaging apparatus is disclosed for diagnosis accommodating an imaging core which has an optical transceiver for transmitting light from a light source toward a vascular tissue and for receiving reflected light from the vascular tissue, and reconstructing a blood vessel image based on interference light data obtained by converting into an electric signal interference light in which measurement light obtained by rotating the imaging core by using a catheter which has an open hole at a distal end portion and reference light separated from the light from the light source are synthesized. The imaging apparatus for diagnosis includes line data generation means for generating line data headed in a radial direction from a rotary center position of the imaging core based on the interference light data, determination means for determining whether or not a foreign substance other than a predetermined liquid enters between the imaging core and an inner surface of the catheter based on distribution of signal strength values in the line data which is generated by the line data generation means, and display means for displaying a message which indicates that entrance of the foreign substance is detected in a case where a determination result of the determination means indicates the entrance of the foreign substance.

According to description of the present application, in a case where a foreign substance such as air and blood other than transparent liquid is present inside a catheter, it is detected and a user is urged to perform priming so that an image having higher accuracy can be reconstructed.

In accordance with an exemplary embodiment, a non-transitory computer readable medium is disclosed containing a computer program having computer readable code embodied to carry out a method of controlling an imaging apparatus for diagnosis accommodating an imaging core which has an optical transceiver for transmitting light from a light source toward a vascular tissue and for receiving reflected light from the vascular tissue, and reconstructing a blood vessel image based on interference light data obtained by converting into an electric signal interference light in which measurement light obtained by rotating the imaging core by using a catheter which has an open hole at a distal end portion and reference light separated from the light from the light source are synthesized, the method of controlling an imaging apparatus for diagnosis comprising: generating line data in a radial direction from a rotary center position of the imaging core based on the interference light data; determining whether or not a foreign substance other than a predetermined liquid enters between the imaging core and an inner surface of the catheter based on distribution of signal strength values in the generated line data; and displaying a message which indicates that entrance of the foreign substance is detected in a case where the entrance of the foreign substance is determined Other features and advantages of the present invention will be clearly described below with reference to the accompanying drawings. In the accompanying drawings, the same reference numerals and signs will be applied to the same or similar configurations.

BRIEF DESCRIPTION OF THE DRAWINGS

The accompanying drawings are incorporated in this description, take part in the configuration, illustrate embodiments of the present invention, and are used to describe the principle of the present invention together with the disclosure thereof.

DETAILED DESCRIPTION

Hereinafter, each of embodiments according to the present disclosure will be described in detail with reference to the accompanying drawings. Since the below-described embodiments are suitable specification examples of the present disclosure, the embodiments are subjected to various types of limitations which are technically preferable. However, the scope of the present disclosure is not limited to the aspects thereof unless otherwise stated in the following description particularly limiting the present disclosure.

Hereinafter, the embodiments of the present disclosure will be described in detail with reference to the accompanying drawings. An imaging apparatus for diagnosis in this description will be described as an imaging apparatus having a function of IVUS and a function of OCT. In addition, the embodiments can be applied to a diagnostic apparatus having only the function of OCT. Therefore, the present disclosure is not limited in regard thereto.

Figure 1:
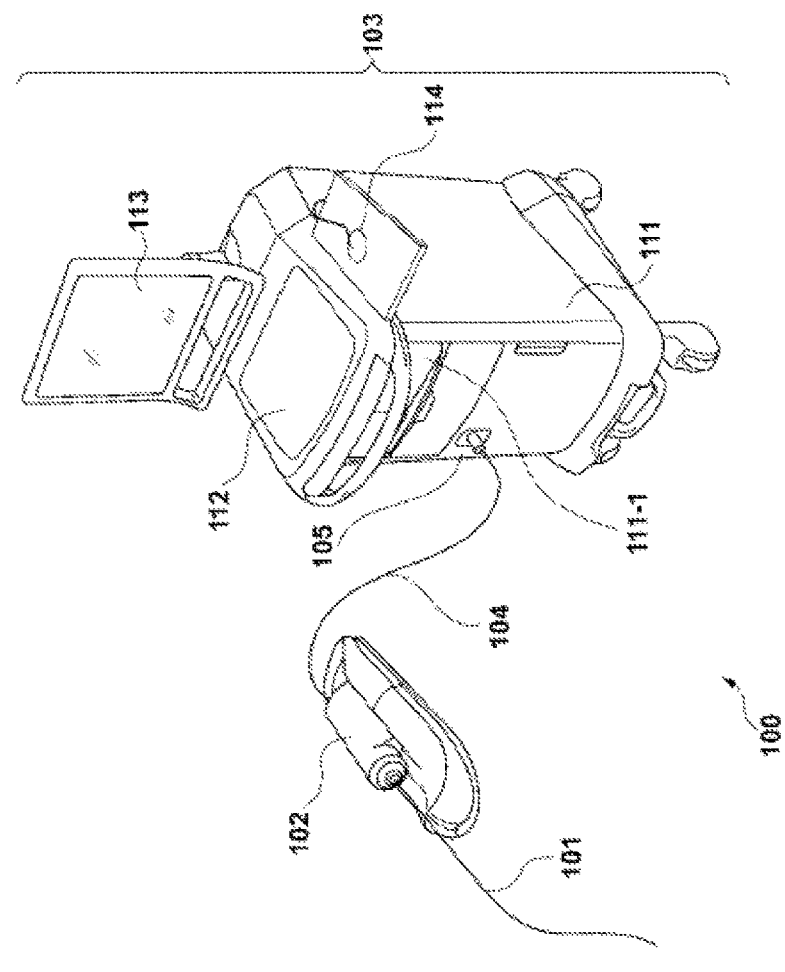
FIG. 1 is a diagram illustrating a configuration of the appearance of an imaging apparatus for diagnosis of the present embodiment.

FIG. 1 is a diagram illustrating a configuration of the appearance of an imaging apparatus 100 for diagnosis according to an embodiment of the present embodiment.

As illustrated in FIG. 1, the imaging apparatus 100 for diagnosis can include a probe 101, a scanner and pull-back unit 102, and an operation control apparatus 103. The scanner and pull-back unit 102 and the operation control apparatus 103 are connected to each other through a cable 104 containing a signal line or an optical fiber via a connector 105.

The probe 101 is directly inserted into a blood vessel. A catheter containing an imaging core provided with an ultrasound wave transceiver which transmits ultrasound waves based on a pulse signal and receives reflected waves from the inside of the blood vessel, and an optical transceiver which continuously transmits sent light (measurement light) to the inside of the blood vessel and continuously receives reflected light from the inside of the blood vessel is inserted into the probe 101. The imaging apparatus 100 for diagnosis measures the state of the inside of a blood vessel by using the imaging core.

The probe 101 is detachably attached to the scanner and pull-back unit 102. The scanner and pull-back unit 102 drives a built-in motor so as to regulate the imaging core inside the catheter being inserted into the probe 101 regarding an axial motion and a rotary motion inside a blood vessel. In addition, the scanner and pull-back unit 102 acquires a signal of the reflected waves which is received by the ultrasound wave transceiver inside the imaging core and the reflected light which is received by the optical transceiver, thereby transmitting the acquired signal and reflected light to the operation control apparatus 103.

The operation control apparatus 103 has a function of inputting various types of setting values and a function of processing ultrasound wave data and interference light data obtained through measurement and displaying various types of vascular images, when performing measurement.

In the operation control apparatus 103, the reference numeral 111 indicates a main body control unit. The main body control unit 111 generates line data from a signal of reflected waves of ultrasound waves obtained through measurement and generates an ultrasound cross-sectional image via interpolation processing. Moreover, the main body control unit 111 causes reflected light from the imaging core and reference light obtained by separating light from a light source to interfere with each other so as to generate the interference light data. The main body control unit 111 generates the line data based on the interference light data and generates a blood vessel cross-sectional image based on optical interference via the interpolation processing.

The reference numeral 111-1 indicates a printer and a DVD recorder, each of which prints a processing result of the main body control unit 111 and stores the processing result as data. The reference numeral 112 indicates an operation panel, and a user inputs various types of setting values and instructions via the operation panel 112. The reference numeral 113 indicates an LCD monitor which is a display device displaying various types of cross-sectional images generated in the main body control unit 111. The reference numeral 114 indicates a mouse, which is a pointing device (a coordinate input device).

Figure 2:
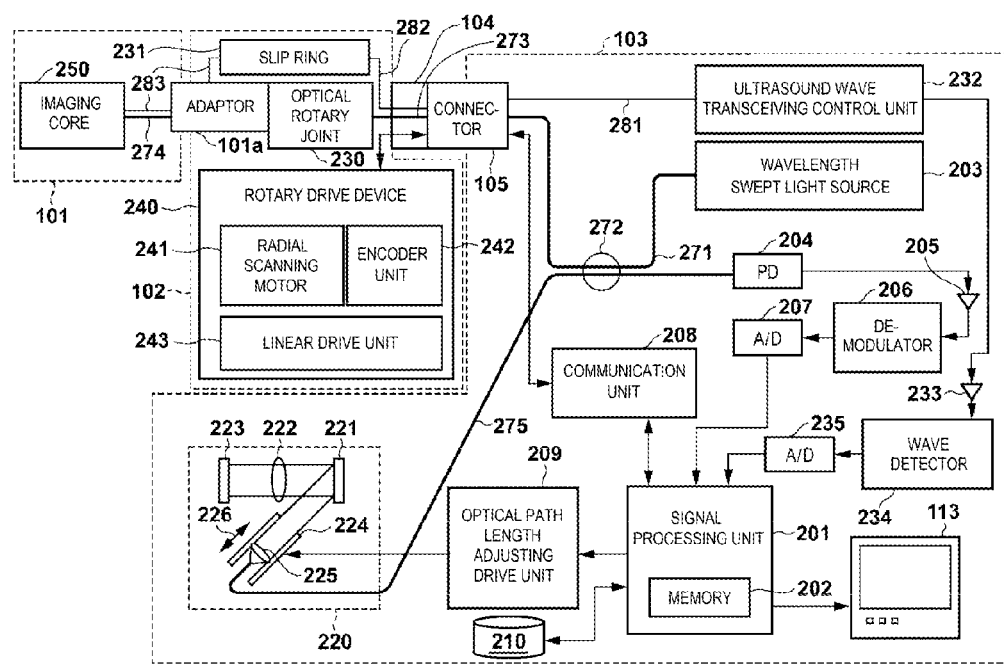
FIG. 2 is a diagram illustrating a configuration of the imaging apparatus for diagnosis.

Subsequently, a functional configuration of the imaging apparatus 100 for diagnosis will be described. FIG. 2 is a block diagram of the configuration of the imaging apparatus 100 for diagnosis. Hereinafter, a functional configuration of the swept source OCT will be described with reference to FIG. 2.

In the diagram, the reference numeral 201 indicates a signal processing unit which takes charge of controlling the imaging apparatus for diagnosis in its entirety and which is configured to have several circuits including a microprocessor. The reference numeral 210 indicates a non-volatile memory device which is represented by a hard disk and stores various types of programs and data files executed by the signal processing unit 201. The reference numeral 202 indicates a memory (RAM) provided inside the signal processing unit 201. The reference numeral 203 indicates a wavelength swept light source which is a light source repeatedly generating light that has a wavelength changing along a time axis within a range set in advance.

Light output from the wavelength swept light source 203 is incident on one end of a first single mode fiber 271 and is transmitted toward a distal side. The first single mode fiber 271 is optically coupled to a fourth single mode fiber 275 by an optical fiber coupler 272 in the middle.

The light which is incident on the first single mode fiber 271 and is emitted toward the distal side farther from the optical fiber coupler 272 is guided to a second single mode fiber 273 via the connector 105. The other end of the second single mode fiber 273 is connected to an optical rotary joint 230 inside the pull-back unit 102.

Meanwhile, the probe 101 has an adaptor 101a so as to be connected to the pull-back unit 102. The probe 101 is stably held by the pull-back unit 102 by connecting the probe 101 to the pull-back unit 102 through the adaptor 101a. Moreover, an end portion of a third single mode fiber 274 which is rotatably contained inside the probe 101 is connected to the optical rotary joint 230. As a result thereof, the second single mode fiber 273 and the third single mode fiber 274 are optically coupled to each other. The other end of the third single mode fiber 274 (a head portion side of the probe 101) is provided with an imaging core 250 which is equipped with the optical transceiver (will be described in detail using FIG. 5) configured to include a mirror and a lens emitting light in a direction of traveling substantially straight forward to a rotary axis.

As a result thereof, the light emitted from the wavelength swept light source 203 is guided to the imaging core 250 provided at an end portion of the third single mode fiber 274 via the first single mode fiber 271, the second single mode fiber 273, and the third single mode fiber 274. The optical transceiver of the imaging core 250 emits the light in a direction of traveling straight forward to the axis of the fiber and receives reflected light thereof. Then, the received reflected light is guided inversely, thereby being returned to the operation control apparatus 103.

Meanwhile, an optical path length adjustment mechanism 220 which performs fine adjustment of the optical path length of the reference light is provided at the end portion on a side opposite to the fourth single mode fiber 275 which is coupled to the optical fiber coupler 272. The optical path length adjustment mechanism 220 functions as optical path length change means for changing the optical path length corresponding to a fluctuation in the length of each probe 101 so as to be able to absorb the fluctuation in the length thereof in a case where the probe 101 is replaced, and the like. Therefore, a collimating lens 225 positioned at the end portion of the fourth single mode fiber 275 is provided on a one-axis stage 224 which is movable in the optical-axis direction thereof as indicated by the arrow 226.

Specifically, the one-axis stage 224 functions as the optical path length change means having a variable range of the optical path length as wide as the fluctuation in the optical path length of the probe 101 can be absorbed in a case where the probe 101 is replaced. Moreover, the one-axis stage 224 also functions as adjustment means for adjusting an offset. For example, even in a case where the distal end of the probe 101 is not in close contact with a surface of a biological tissue, it is possible to set a state of being interfered with by the reflected light from a surface position of the biological tissue by performing fine changing of the optical path length through the one-axis stage.

Light of which the optical path length is subjected to fine adjustment through the one-axis stage 224 and which is reflected by a mirror 223 via a grating 221 and a lens 222 is guided to the fourth single mode fiber 275 again and is mixed with light obtained from the second single mode fiber 273 side by the optical fiber coupler 272, thereby being received by a photo diode 204 as interference light.

The interference light received by the photo diode 204 as described above is subjected to photoelectric conversion, thereby being input to a demodulator 206 after being amplified by an amplifier 205. The demodulator 206 performs demodulation processing of extracting only a signal component of the interference light, and an output thereof is input to an A/D converter 207 as an interference light signal.

In the A/D converter 207, the interference light signal is sampled at 90 MHz at as many as 2,048 points, for example, thereby generating digital data (interference light data) for one line. The sampling frequency is set to 90 MHz on the premise that approximately 90% of a periodical cycle (25 μsec) of wavelength sweeping is extracted as the digital data at 2,048 points in a case where the repetition frequency of the wavelength sweeping is set to 40 kHz. However, the sampling frequency is not particularly limited thereto.

The interference light data generated by the A/D converter 207 in a line unit is input to the signal processing unit 201 and is temporarily stored in the memory 202. The signal processing unit 201 generates data (line data) in a depth direction by causing the interference light data to be subjected to frequency resolution through fast fourier transform (FFT). Then, the generated data is subjected to coordinate conversion so as to construct an optical cross-sectional image at each position in a blood vessel, thereby outputting the constructed image to the LCD monitor 113 at a predetermined frame rate.

The signal processing unit 201 is also connected to an optical path length adjusting drive unit 209 and a communication unit 208. The signal processing unit 201 performs controlling of the position (controlling of the optical path length) of the one-axis stage 224 via the optical path length adjusting drive unit 209.

The communication unit 208 can include several built-in drive circuits and communicates with the pull-back unit 102 while being under the control of the signal processing unit 201. Specifically, drive signals are supplied to a radial scanning motor for rotating the third single mode fiber by using the optical rotary joint inside the pull-back unit 102, signals are received from an encoder unit 242 for detecting a rotation position of the radial motor, and drive signals are supplied to the linear drive unit 243 for pulling the third single mode fiber 274 at a predetermined speed.

The above-described processing of the signal processing unit 201 is also realized as a computer executes a predetermined program.

In the above-described configuration, when the probe 101 is positioned at a blood vessel position (the coronary artery) which is a diagnostic target of a patient, transparent flushing liquid is released inside the blood vessel toward the distal end of the probe 101 through a guiding catheter or the like in accordance with an operation of a user. The operation is performed in order to eliminate the influence of blood. When the user inputs instructions to start scanning, the signal processing unit 201 drives the wavelength swept light source 203, thereby driving a radial scanning motor 241 and the linear drive unit 243 (hereinafter, processing of irradiation and reception of light performed by driving the radial scanning motor 241 and the linear drive unit 243 will be referred to as scanning). As a result thereof, wavelength swept light is supplied to the imaging core 250 from the wavelength swept light source 203 through the above-described route. In this case, since the imaging core 250 at the position of the distal end of the probe 101 moves along the rotary axis while rotating, the imaging core 250 emits light to a vascular lumen surface and receives the reflected light thereof while rotating and moving along the vascular axis.

Figure 3:
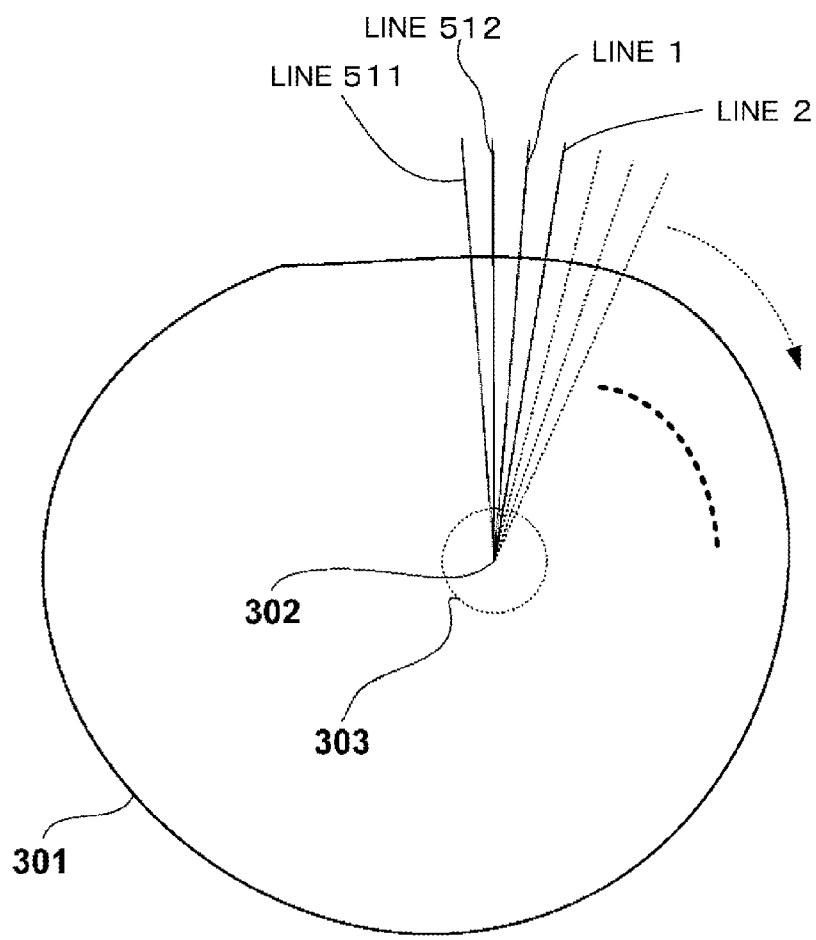
FIG. 3 is a diagram for describing reconstruction processing of a cross-sectional image.

Here, processing related to generation of one optical cross-sectional image will be described with reference to FIG. 3. FIG. 3 is a diagram for describing reconstruction processing of a cross-sectional image of a vascular lumen surface 301 on which the imaging core 250 is positioned. The measurement light is transmitted and received multiple times while the imaging core 250 makes one rotation (360 degrees). Data of one line in a direction of light irradiation can be obtained through transceiving of light performed once. Therefore, for example, by performing transceiving of light 512 times during one rotation, 512 items of the line data radially extending from a rotary center 302 can be obtained.

Figure 4:
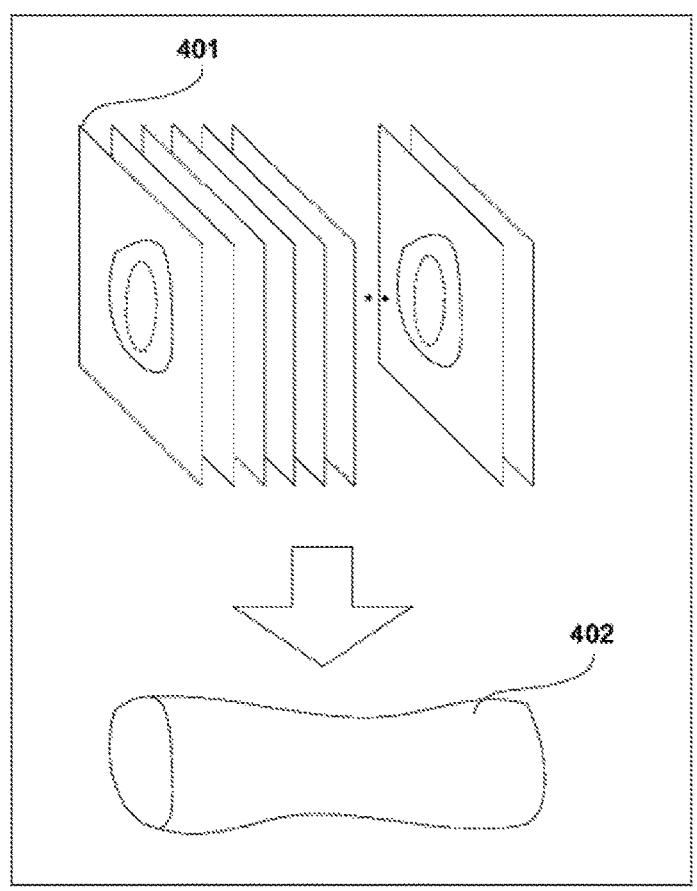
FIG. 4 is a diagram illustrating an example of three-dimensional model data of a reconstructed blood vessel.

512 items of the line data are close to one another in the vicinity of the rotary center position and are estranged from one another while being separated from the rotary center position. Therefore, pixels in the empty space of each line are generated by performing known interpolation processing so as to generate two-dimensional cross-sectional images which can be visually recognized by a person. Generated two-dimensional cross-sectional images 401 are connected to each other in a line along the vascular axis as illustrated in FIG. 4 so that a three-dimensional blood vessel image 402 can be obtained. The center position of the two-dimensional cross-sectional images coincides with the rotary center position of the imaging core 250. However, note that, the center position thereof is not the center position of the blood vessel cross section. In addition, even though it is modest, light is reflected by the lens surface of the imaging core 250, and the surface of the catheter. Therefore, as indicated by the reference numeral 303 in the diagram, several concentric circles can be generated with respect to the rotary central axis.

Subsequently, a configuration and contents of processing related to image forming performed by using ultrasound waves will be described.

Scanning performed by using ultrasound waves is performed at the same time as the optical interference scanning described above. In other words, while scanning is performed so that the imaging core 250 rotates and moves inside a catheter sheath of the probe 101, ultrasound waves are emitted from the ultrasound wave transceiver contained in the imaging core 250 and the reflected waves thereof are detected. Therefore, there is a need to generate an electrical driving signal for driving the ultrasound wave transceiver contained in the imaging core 250 and to receive a detection signal of ultrasound waves output by the ultrasound wave transceiver. Transmitting of the drive signals and receiving of the detected signals are performed by an ultrasound wave transceiving control unit 232. The ultrasound wave transceiving control unit 232 and the imaging core 250 are connected to each other via signal line cables 281, 282, and 283. Since the imaging core 250 rotates, the signal line cables 282 and 283 are electrically connected to each other via a slip ring 231 provided inside the pull-back unit 102. In the diagram, the signal line cables 281 to 283 are illustrated, as if the cables are connected through one line. However, actually, multiple signal lines are contained.

The ultrasound wave transceiving control unit 232 is in operation under the control of the signal processing unit 201 and drives the ultrasound wave transceiver contained in the imaging core 250, thereby generating pulse waves of ultrasound waves. The ultrasound wave transceiver converts the reflected waves from a vascular tissue into an electrical signal, thereby supplying the converted signal to the ultrasound wave transceiving control unit 232. The ultrasound wave transceiving control unit 232 outputs the received ultrasound wave signal to an amplifier 233, thereby amplifying the output signal. Thereafter, the amplified ultrasound wave signal is supplied to the signal processing unit 201 as the ultrasound wave data via a wave detector 234 and an A/D converter 235, thereby being temporarily stored in the memory 202. In the A/D converter 235, the ultrasound wave signal output by a wave detector 454 is sampled at 30.6 MHz at as many as 200 points, thereby generating digital data (ultrasound wave data) for one line. Here, the frequency of 30.6 MHz is calculated on the premise that the sampling is performed at 200 points with respect to the depth of 5 mm when the speed of sound is considered to be 1,530 m/sec. However, the sampling frequency is not particularly limited thereto.

The signal processing unit 201 converts the ultrasound wave data stored in the memory 202 into a gray scale, thereby generating an ultrasound wave cross-sectional image of each position inside the blood vessel.

Subsequently, the structure of the catheter containing the imaging core 250 in the probe 101 will be described in accordance with FIG. 5.

Figure 5:
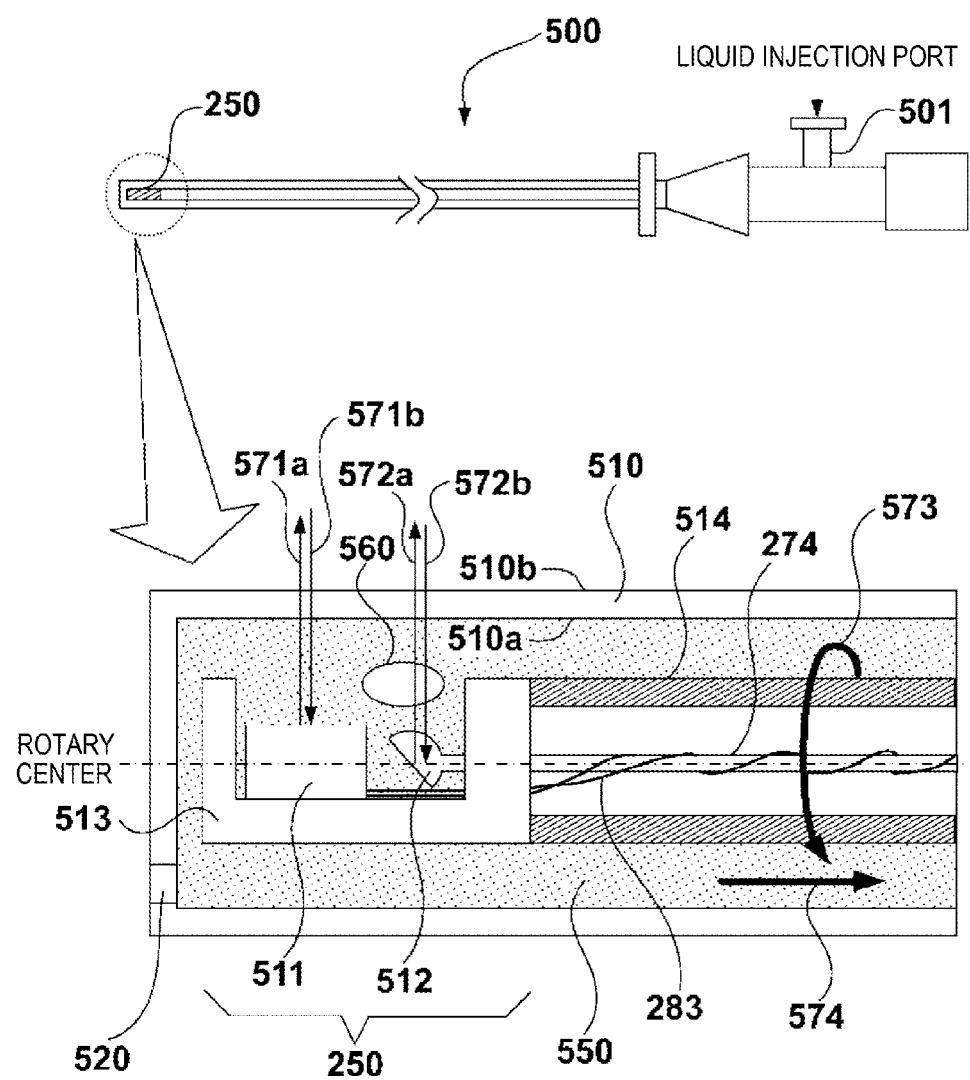
FIG. 5 is a cross-sectional view illustrating a structure of a catheter of the embodiment.

The reference numeral 500 in FIG. 5 is the catheter of the embodiment. In the vicinity of the proximal end (the end portion connected to the pull-back unit 102) of a catheter 500, an injection port 501 is provided for injecting transparent liquid 550 (a physiological salt solution) into the catheter sheath. The catheter 500 contains the above-described third single mode fiber 274 and the signal line cable 283. However, the proximal end of the catheter 500 is configured to have a shield structure so that the liquid does not leak.

In the distal end portion of the catheter 500, there is provided a priming hole 520 for discharging an air bubble generated when the inside of the catheter sheath is filled with the liquid 550. In addition, a catheter sheath 510 of the catheter 500 is configured to be made from a transparent material. The imaging core 250 which is rotatable while being movable along the catheter 500 is contained inside the catheter 500. The imaging core 250 is configured to include an ultrasound wave transceiver 511, an optical transceiver 512, and a housing 513 containing it. In addition, the housing 513 is supported by a drive shaft 514. The drive shaft 514 is configured to be made from a material having characteristics of being soft and being able to favorably transmit rotations, for example, a material such as a multiplex-multilayer contact coil formed of metal wire such as stainless steel. The signal line cable 283 and the third single mode fiber 274 are contained inside the drive shaft 514.

In addition, the housing 513 has a notch portion at a portion of the cylindrical metal pipe thereof. The ultrasound wave transceiver 511 and the optical transceiver 512 transmit and receive ultrasound waves and light via the notch portion.

The ultrasound wave transceiver 511 emits ultrasound waves in a direction of the illustrated arrow 571a in response to the pulse signal applied from the signal line cable 283, detects the reflected waves from the vascular tissue indicated by the arrow 571b, thereby outputting the detected waves through the signal line cable 283 as an electrical signal.

The optical transceiver 512 is provided at the distal portion of the third single mode fiber 274 and is formed to have a hemispherical body shape obtained by cutting a spherical body at an angle of substantially 45 degrees with respect to the perpendicular surface of FIG. 5. A mirror portion is formed on the slope thereof. In addition, the optical transceiver 512 also functions as a lens by having the hemispherical body shape. Light supplied via the third single mode fiber 274 is reflected by the mirror portion and is emitted toward the vascular tissue along the illustrated arrow 572a. The reflected light from the vascular tissue as indicated by the illustrated arrow 572b is received and is reflected by the mirror portion, thereby returning the reflected light to the third single mode fiber 274.

As described above, since the pull-back unit 102 drives the radial scanning motor 241 thereof and the linear drive unit 243 during the scanning, the drive shaft 514 rotates along the arrow 573 and moves along the arrow 574. As a result thereof, the imaging core 250 performs emission of ultrasound waves and detection of the reflected waves thereof and emission of light and detection of the reflected light thereof while rotating and moving in the axial direction thereof.

The catheter sheath 510 performs a preoperative priming operation. In other words, the catheter sheath 510 performs an operation of filling the inside of the catheter sheath 510 with the liquid 550 by injecting the liquid 550 through the liquid injection port 501 and discharging air inside thereof through the priming hole 520. Meanwhile, a problem regarding a case where the priming operation is insufficient and an air bubble 560 is present will be examined.

In the reconstruction processing of a vascular image utilizing optical interference and the reconstruction processing of a vascular image utilizing ultrasound waves, a known medium (for example, a physiological salt solution in the embodiment) fills the space between the catheter sheath 510 and the imaging core 250. In other words, the reconstruction processing of a vascular image is performed on the premise that the propagation speed of ultrasound waves and light between the catheter sheath 510 and the imaging core 250 is known. When a medium other than the known medium is present between the catheter sheath 510 and the imaging core 250, the propagation speed of sound waves or light at the portion thereof becomes unpredictable so that turbulence or an artifact is generated in the image to be reconstructed. Particularly, since most of ultrasound waves are reflected by an interface between gas such as air and liquid such as a saline, an image which is reconstructed by utilizing the IVUS can extremely deteriorate.

Therefore, notifying a user that the priming is insufficient in a case where an air bubble is present can be important. Hereinafter, the principle of detecting an air bubble will be described.

Light supplied to the third single mode fiber 274 is reflected by the mirror portion of the optical transceiver 512 and is emitted in a direction (the arrow 572a) orthogonal to the moving direction (the arrow 574) of the imaging core 250. Light has properties in which light is reflected by the border surface between two mediums respectively having refractive indexes different from each other. Therefore, even though most of light reflected by the mirror portion of the optical transceiver 512 is emitted to the outside of the catheter sheath 510, a portion of the light is reflected by the lens surface of the optical transceiver 512 itself, an inner side surface 510a of the catheter sheath 510, and an outer side surface 510b of the catheter sheath 510 due to the properties thereof.

Figure 6A:
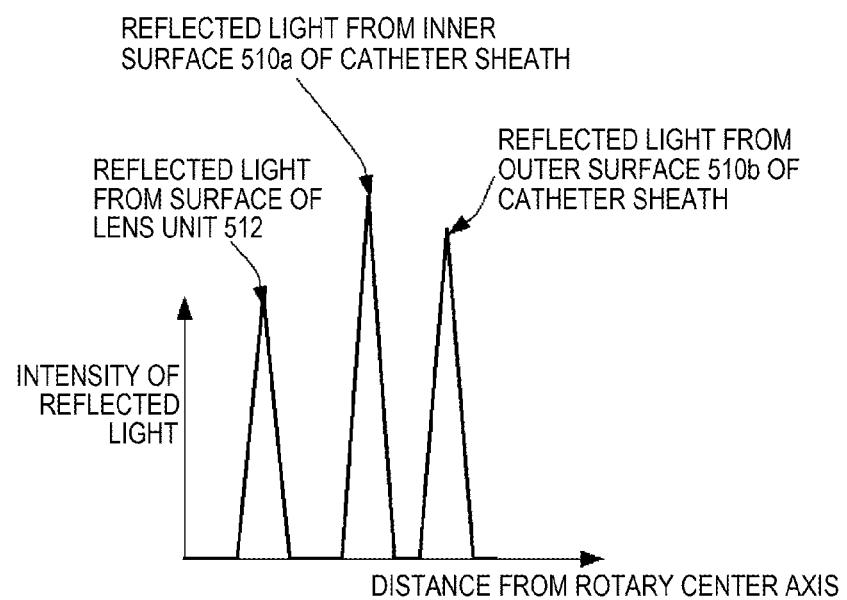
FIG. 6A is a diagram for describing the principle of detecting an air bubble and blood.

Here, a case where only the liquid 550 is present between the optical transceiver 512 and the inner side surface of the catheter sheath 510, and no air bubble is present will be examined. Regarding this case, FIG. 6A illustrates a result in which pixels (luminosity values) configuring the line data obtained by performing FFT are arranged from the rotary central axis. The illustrated horizontal axis corresponds to a distance from the rotary center position, and the vertical axis indicates luminance at the position thereof. As illustrated in the diagram, three peaks such as the position of the lens surface of the optical transceiver 512, the position of the inner side surface 510a of the catheter sheath 510, and the position of the outer side surface 510b are detected in order from the position close to the rotary center position. Moreover, the luminance of the trough between the peaks at the position of the lens surface of the optical transceiver 512 and the position of the inner side surface 510a of the catheter sheath 510 is zero or is substantially equivalent to zero. The reason thereof is that the liquid 550 is transparent. A distance from the position of the lens surface of the optical transceiver 512 to the outer side surface 510b of the catheter sheath 510 corresponds to a known value obtained by subtracting a distance from the rotary center to the lens surface of the optical transceiver 512, from the radius of the catheter. Therefore, the three peaks within the known range are considered to indicate the lens surface of the optical transceiver 512, the inner side surface 510a of the catheter sheath 510, and the position of the outer side surface 510b.

Figure 6B:
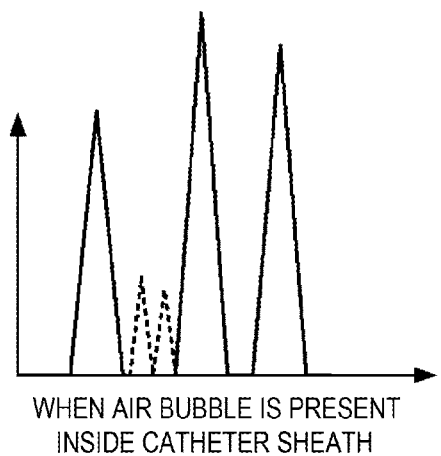
FIG. 6B is another diagram for describing the principle of detecting an air bubble and blood.

Subsequently, as illustrated in FIG. 5, a case where the air bubble 560 is present between the optical transceiver 512 and the inner side surface of the catheter sheath 510 will be examined. Regarding this case, light which has passed through the lens of the optical transceiver 512 passes through at least one of the border surfaces between the air bubble 560 and the liquid 550 until the light arrives at the inner side surface 510a of the catheter sheath 510. If the number of air bubbles increases, the border surfaces corresponding to the number of air bubbles are present. Thus, a reflection phenomenon occurs on each of the border surfaces. Therefore, in the line data obtained through the FFT of the signal processing unit 201, several peaks are generated at portions of the troughs between the optical transceiver 512 and the inner side surface of the catheter sheath 510 as illustrated in FIG. 6B.

Therefore, it is possible to determine that an air bubble is present when luminance equal to or greater than a threshold value set in advance is present within a range of the troughs between the optical transceiver 512 and the inner side surface of the catheter sheath 510, that is, the troughs of which the luminance are supposed to be zero originally.

The propagation speed of light is higher in air than in liquid. Therefore, a time taken for being propagated between the optical transceiver 512 and the inner side surface of the catheter sheath 510 is shorter in a case where an air bubble is present therebetween compared to a case where only the liquid 550 is present therebetween. Therefore, the peaks in FIG. 6B indicating the positions of the inner side surface 510a and the outer side surface 510b of the catheter sheath 510 appear and are found at the positions, which are slightly shifted to the left side (the rotary center position) from the positions in FIG. 6A. In the embodiment, the conditions for specifying the peaks of the lens surface of the optical transceiver 512, and the inner side surface 510a and the outer side surface 510b of the catheter sheath 510 are set as follows.

(1) The optical transceiver 512 is provided at the distal portion of the third single mode fiber 274. Regardless of the presence and the absence of an air bubble, the first position by which light supplied to the third single mode fiber 274 is reflected is the position of the lens surface of the optical transceiver 512. Therefore, among the peaks generated in the line data, which is obtained through the FFT of the signal processing unit 201, a peak which is generated on a side closest to the rotary center side corresponds to the reflection on the lens surface of the optical transceiver 512. In addition, the distance from the rotary center to the lens surface of the optical transceiver 512 is fixed (known).

(2) The apparent distance from the lens surface of the optical transceiver 512 to the outer side surface 510b of the catheter sheath is maximized in a case where only the liquid 550 is present therebetween, and the maximum distance is equivalent to a value obtained by subtracting a distance (known) from the rotary center to the lens surface of the optical transceiver 512, from the radius of the outer side surface 510b of the catheter sheath 510. In addition, the apparent distance from the lens surface of the optical transceiver 512 to the outer side surface 510b of the catheter sheath is minimized in a case where only gas (air) is present therebetween. Therefore, the peak between the maximum distance and the minimum distance is considered to indicate the outer side surface 510b of the catheter sheath. Moreover, the range from the peak position of the outer side surface 510b of the catheter sheath to the rotary center position, that is, the range corresponding to the thickness of the catheter sheath 510 is occupied by the material of the catheter sheath 510, and no peak is generated therein. According to the conditions, the peak position of the outer side surface 510b of the catheter sheath 510 can be specified at sufficient accuracy.

(3) In a case where the peak position of the outer side surface 510b of the catheter sheath 510 can be specified, a position separated from the peak position of the outer side surface 510b toward the rotary center position by a distance corresponding to the thickness of the catheter sheath 510 becomes the peak position of the inner side surface 510a of the catheter sheath 510.

In an HDD 210, pixel values (hereinafter, referred to as reference pixel values) C1, C2, and so on to Cm, which become references between the peak position of the lens surface of the optical transceiver 512 and the peak position of the inner side surface 510a of the catheter sheath 510 in a state of being filled with only the liquid 550 and having no air bubble, are stored in advance.

In a case where three peaks are obtained through actual measurement under the above-described conditions, pixel values (luminance) P1, P2, P3, and so on to Pn between the peak position of the lens surface of the optical transceiver 512 and the peak position of the inner side surface 510a of the catheter sheath 510 are obtained from the line data.

Here, m and n can be substantially equivalent to each other. However, since the propagation speed may vary due to the influence of entrance of air bubble and the like, m and n are not necessarily the same as each other. The horizontal axis indicates the pixel position, and the vertical axis indicates the luminosity value. An approximation curve connecting the reference pixel values C1, C2, and so on to Cm is subjected to the interpolation processing (multiplication with respect to the horizontal axis by n/m times), thereby obtaining interpolation reference pixel values C'1, C'2, and so on to C'n. As a result thereof, the same number as the number n of the actual measurement pixel values is obtained, and thus, an evaluation value S indicating the dissimilarity therebetween is obtained in accordance with the following Expression (1).

$$S=\Sigma|C'i-Pi| \qquad (1)$$

Here, $\Sigma$ indicates the sum of i=1, 2, and so on to n. |x| indicates the absolute value of x. When the evaluation value S and a threshold value T set in advance are compared to each other, and there is a relationship of S>T, it is determined that an air bubble is present. In a case where S≤T, it is determined that no air bubble is present.

When the threshold value T is set to have a small value, a stricter determination reference can be established. In addition, when the threshold value T is set to have a significant value, an alleviated determination reference can be established. In accordance with an exemplary embodiment, the permissible range with respect to a foreign substance can be changed by the signal processing unit 201 in accordance with the circumstances. For example, the permissible range can be changed via the operation control apparatus 103 by inputting the numerical values of the threshold value T displayed in the LCD monitor 113 by using the operation panel 112 and the mouse 114.

The absolute value is applied in the above-referenced case. However, the evaluation value S may be obtained through the following Expression (2).

$$S=\Sigma(C'i-Pi)^2 \qquad (2)$$

In addition, when the liquid 550 is transparent liquid, and the pixel value of all the reference values may be considered to be zero, the evaluation value S may be obtained through the following Expression (3).

$$S = \Sigma P_i \quad (3)$$

The signal processing unit 201 checks for an air bubble in the catheter 500 before performing the pull-back processing, thereby controlling the procedure to proceed to the next processing (pull-back scanning) in only a case where it is determined that no air bubble is present.

The processing regarding detection of an air bubble inside the catheter 500 has been described above. However, there is a case where blood flows into the catheter 500 through the priming hole 520 when the probe 101 is actually inserted into a blood vessel of a patient and scanning is performed. Hereinafter, a reason of blood inflow and a problem thereof will be examined.

As illustrated in FIG. 5, when the scan processing is executed, the pull-back unit 102 is driven so that the imaging core 250 rotates along the arrow 573 inside the catheter sheath 510 and moves along the arrow 574. Then, the imaging core 250 and the drive shaft 514 function like pistons, and the inside of the catheter 500 is under negative pressure. This is one of the reasons that blood flows into the catheter 500 through the priming hole 520.

Generally, in the scan processing using optical interference, in order to reduce the influence of blood, transparent flushing liquid is released inside a blood vessel toward the distal end of the probe 101 through the guiding catheter during the scanning. However, it is not always possible to eliminate blood, and a little amount of blood sometimes flows into the catheter 500. Particularly, in a case where several rounds of scanning are performed with respect to a target lesion, there can be a high possibility that blood flows into the catheter 500 due to blood pressure during the standby time between each step of the scan processing. Since blood is opaque liquid, when blood flows into the catheter 500, an image reconstructed by utilizing optical interference becomes blurred.

In the present embodiment, it is also detected that blood flows into the catheter 500, and upon detection of it, a message of urging a user to perform priming can be displayed.

Figure 6C:
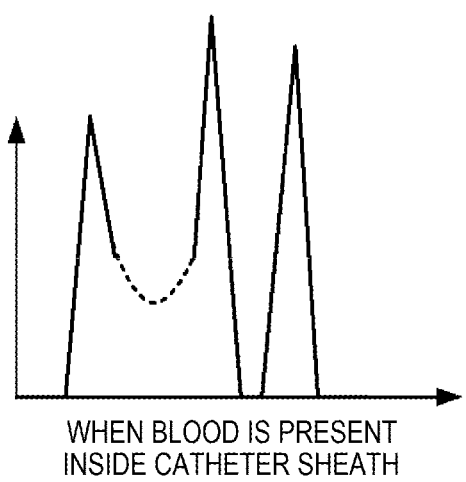
FIG. 6C is another diagram for describing the principle of detecting an air bubble and blood.

When blood flows into the catheter 500, opaque liquid is present between the peak position of the lens surface of the optical transceiver 512 and the peak position of the inner side surface 510a of the catheter sheath 510. Therefore, the luminosity value of the line data in the vicinity of the imaging core 250 exhibits the distribution as illustrated in FIG. 6C. In other words, the trough between the peak position of the lens surface of the optical transceiver 512 and the peak position of the inner side surface 510a of the catheter sheath 510 becomes shallow.

The conditions for determining the peak position of the lens surface of the optical transceiver 512, the peak position of the inner side surface 510a of the catheter sheath 510, and the peak position of the outer side surface 510b may be the same as the conditions (1) to (3) for detecting an air bubble. Moreover, an algorithm which is exactly the same as that in detecting an air bubble can be applied to the conditions for determining whether or not the opaque liquid (blood) is present.

Figure 7A:
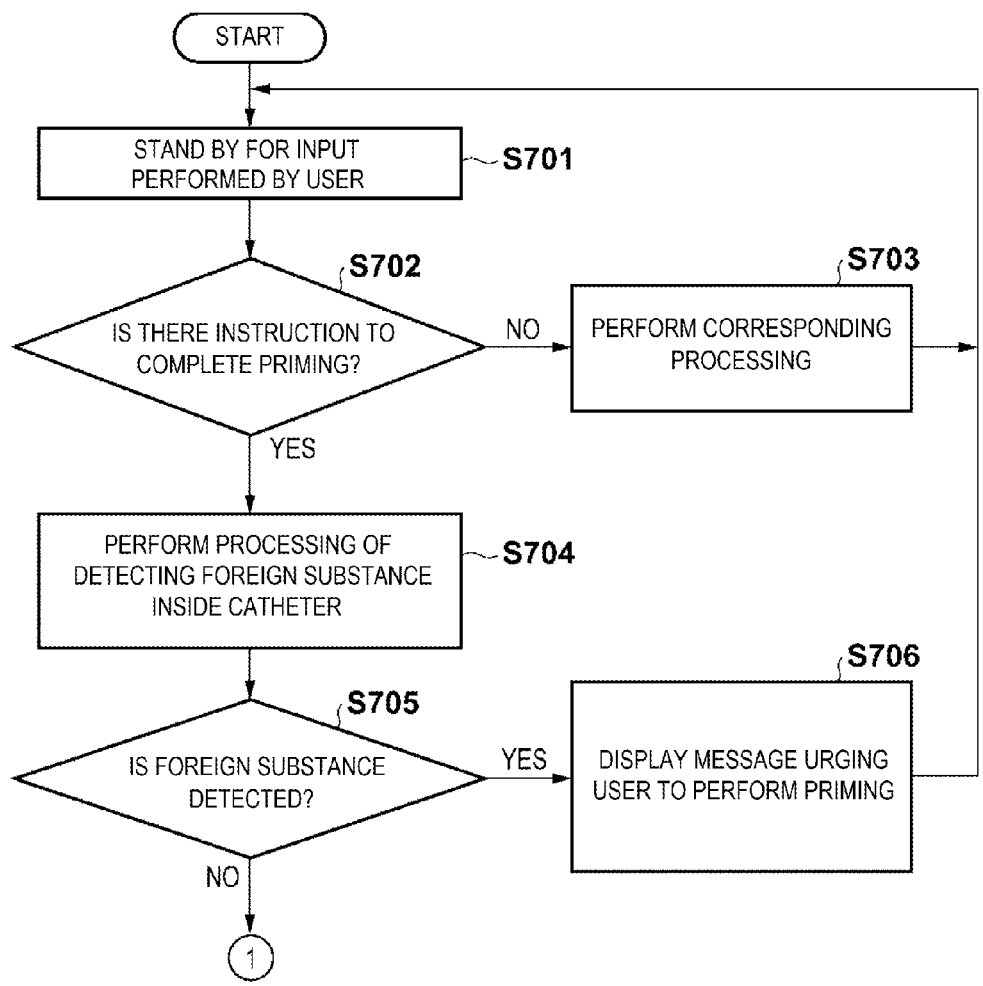
FIG. 7A is a flow chart illustrating a processing procedure of the imaging apparatus for diagnosis of the embodiment.
Figure 7B:
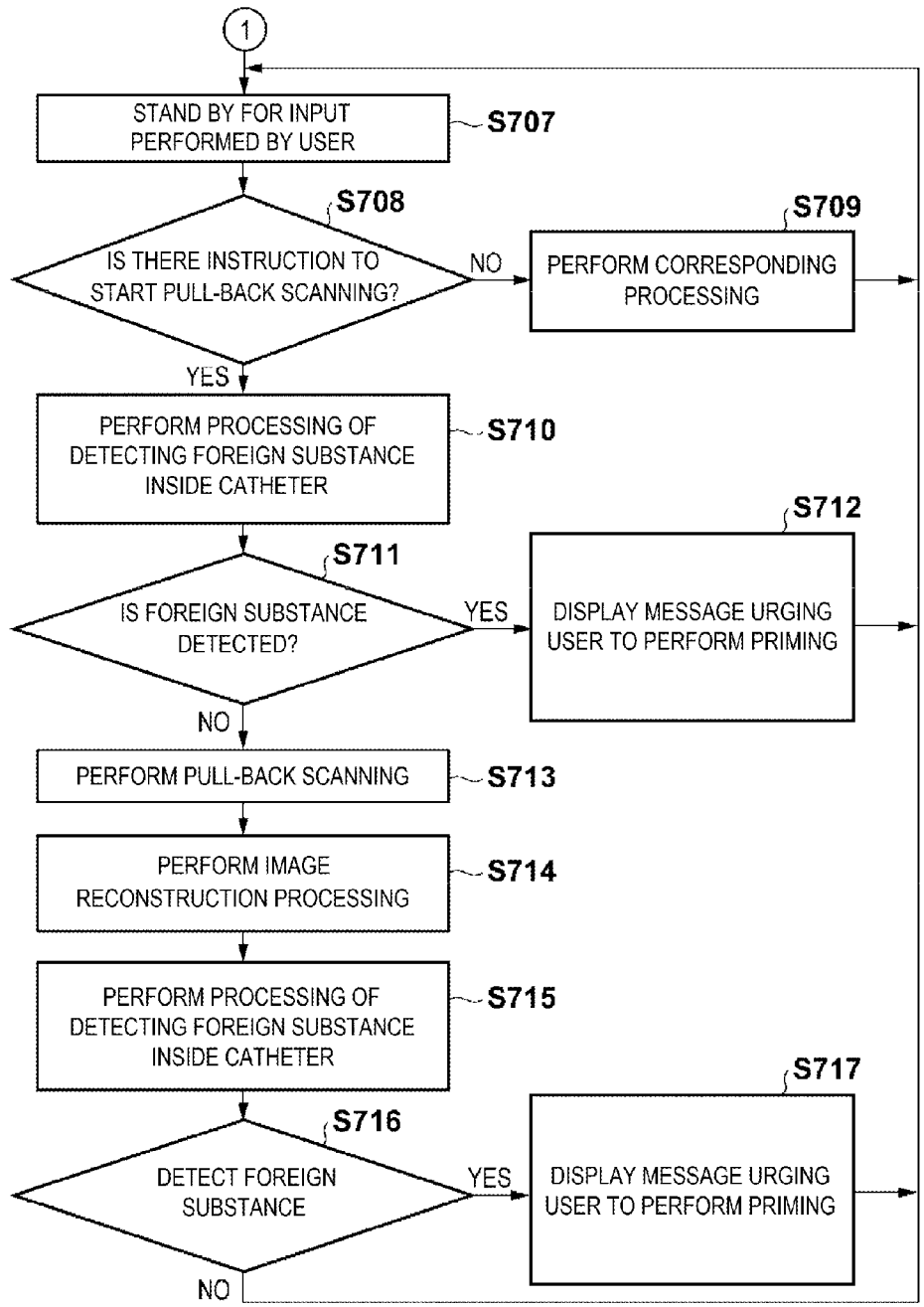
FIG. 7B is a flow chart illustrating another processing procedure of the imaging apparatus for diagnosis of the embodiment.

Hereinbefore, the principle of detecting an air bubble and blood inside the catheter 500 in the embodiment and countermeasure processing thereof are described. However, the signal processing unit 201 performs processing in accordance with the flow charts in FIGS. 7A and 7B.

In Step S701, the signal processing unit 201 waits for an input performed by a user through the operation panel 112 and the mouse 114. When there is an input, in Step S702, it is determined whether or not the input is instruction indicating that the priming work is completed. In a case where the input is other than the instruction indicating the completion of the priming, the processing proceeds to Step S703, thereby performing corresponding processing. Meanwhile, in a case where the input is the instruction indicating the completion of the priming work, inspecting whether or not a foreign substance (air bubble) is no longer present is performed in Step S704. Although the processing has already been described, the processing will be simply described again as follows.

The signal processing unit 201 drives the wavelength swept light source 203 and drives the radial scanning motor with respect to the pull-back unit 102, thereby rotating the imaging core 250 for a predetermined period of time. In this case, the linear drive unit 243 is not driven. As a result thereof, the imaging core 250 starts to rotate as indicated by the arrow 573 in FIG. 5. However, since the linear drive unit 243 is not driven, the imaging core 250 does not move along the arrow 574.

The signal processing unit 201 stores the interference light data obtained by synthesizing light detected by the optical transceiver 512 of the imaging core 250 and the reference light in the memory 202 and performs the FFT, thereby generating multiple items of the line data (desirably the line data for 360 degrees). The multiple items of the line data are analyzed. In addition, positions of the lens surface of the optical transceiver 512, and the inner side surface 510a and the outer side surface 510a of the catheter sheath are determined for each item of the line data in accordance with the above-referenced conditions. Then, the evaluation value S of entrance of a foreign substance is obtained from a pixel group between a position indicating the lens surface of the optical transceiver 512 and a position indicating the inner side surface 510a of the catheter sheath, and a reference pixel group in the line data. It is determined that whether or not the evaluation value S is greater than a threshold value which is set in advance. In a case where one item of the line data which is greater than the threshold value is present, it is determined that a foreign substance (air bubble) is present inside the catheter 500. In a case where not even one item of the line data which is greater than the threshold value is present, it is determined that no foreign substance is present.

In Step S705, it is determined whether or not the foreign substance inspection indicates the presence of a foreign substance. In a case of indicating the presence of a foreign substance, the processing proceeds to Step S706, a message indicating that the priming is insufficient is displayed in the LCD monitor 113, and the processing returns to Step S701.

In a case where it is determined that no foreign substance is present, a user performs various types of setting included in the pull-back processing and inserts the probe 101 into a blood vessel of a patient, thereby performing work of positioning the distal end at the coronary artery or the like. In addition, when the probe 101 can be moved to the position thereof, instruction to start the pull-back scanning is input through the operation panel 112. In addition, in some cases, instruction to end the processing may be input.

When any instruction is input through the operation panel 112 (Step S707), the signal processing unit 201 determines whether or not the instruction is instruction to start the pull-back scanning (Step S708). In a case where the input is other than the instruction indicating the pull-back scanning, the corresponding processing is performed in Step S709.

Meanwhile, in a case where it is determined that the input is the instruction to start the pull-back scanning, the signal processing unit 201 performs detection of a foreign substance (in this case, blood) again before the actual pull-back processing starts (Step S710). The foreign substance detection processing is the same as that in Step S704 which has already been described. The foreign substance detection processing is performed by driving the radial scanning motor while not driving the linear drive unit 243 of the pull-back unit 102. In Step S711, in a case where it is determined that a foreign substance is present, there is a possibility that no clear image can be obtained even though the pull-back scanning is performed without change. Therefore, the processing proceeds to Step S712, a message of urging a user to perform the priming is displayed in the LCD monitor 113, and the processing returns to Step S707.

In a case where it is determined that no foreign substance is present, the processing proceeds to Step S713, thereby starting the pull-back scanning processing. In other words, the wavelength swept light source 203 is driven and the ultrasound wave transceiving control unit 232 is controlled, thereby starting generating and receiving of ultrasound waves. In addition, the radial scanning motor 241 and the linear drive unit 243 are driven. The radial scanning motor 241 rotates the imaging core 250 at a speed set in advance. The linear drive unit 243 moves the imaging core 250 at a predetermined speed based on the set distance. The imaging core 250 is rotated at a speed set in advance and is moved at a predetermined speed by the set distance. In the meantime, since the interference light data and the ultrasound wave data can be obtained from the A/D converters 207 and 235, the data are accumulated in the memory 202.

When the pull-back scanning processing ends, in Step S714, the signal processing unit 201 performs the FFT with respect to the interference light data and the ultrasound wave data accumulated in the memory 202, constructs the line data, performs processing of generating the cross-sectional images throughout the entire area along the pull-back vascular axis, and performs processing of displaying the result in the LCD monitor 113.

In Step S715, the line data, which has already been constructed in the memory 202 is analyzed, and it is determined whether or not a foreign substance (blood) flows into the catheter 500. The determination is substantially the same as that in Step S704. In Step S716, in a case where it is determined that a foreign substance (blood) flows into the catheter 500, in Step S717, the possibility that an image obtained by performing the scanning deteriorates due to the influence of the blood flow, and a message urging a user to perform the priming once in a case of continuously performing the scanning are displayed in the LCD monitor 113. Then, the processing returns to Step S707.

According to the present embodiment which have been described above, in the imaging apparatus for diagnosis utilizing optical interference, in a case of obtaining a vascular image after transparent liquid set inside the catheter in advance is contained, it is determined whether or not a medium other than the transparent liquid is present inside the catheter. In a case where the transparent liquid is present, a user is urged to perform the priming, and thus, an image having high accuracy can be obtained.

In the above-described embodiment, description has been given regarding an example of the diagnostic apparatus having both functions of the IVUS and the OCT. However, the embodiment may be applied to the diagnostic apparatus having only the function of the OCT. In addition, in the above-described embodiment, in a case where it is determined that a foreign substance (air bubble) is present, description has been given regarding an example in which notification is issued in a display screen by causing the LCD monitor 113 to display a message indicating that a foreign substance (air bubble) is present. However, the embodiment is not limited thereto. The notification may be issued by notification means such as an alarm or a sound. Moreover, the notification may be issued by both the screen displaying and the notification means such as an alarm or a sound. It is possible to more reliably allow a user to know the circumstances by notifying the user both visually and acoustically.

As it can be understood from the above-described embodiment, the processing of the air bubble inspection and blood inspection is performed by the signal processing unit 201 which is configured to be a microprocessor. Since the microprocessor realizes the function by executing the program, the program is naturally included in the scope of the present disclosure as well. In addition, generally, the program is stored in a computer readable storage medium such as CD-ROM or DVD-ROM, and the program is set to a reading device (a CD-ROM drive) included in the computer, thereby being executable by being copied or installed in the system. Therefore, the computer readable storage medium is included in the scope of the present disclosure as well.

The present invention is not limited to the embodiments described above, and thus, various changes and modifications can be made without departing from the gist and the scope of the present invention. Therefore, in order to make the scope of the present invention be public, the following claims are attached herein.

The detailed description above describes to an imaging apparatus for diagnosis, a method of controlling the same, a program, and a computer readable storage medium. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus for diagnosis accommodating an imaging core which has an optical transceiver for transmitting light from a light source toward a vascular tissue and for receiving reflected light from the vascular tissue, and reconstructing a blood vessel image based on interference light data obtained by converting into an electric signal interference light in which measurement light obtained by rotating the imaging core by using a catheter which has an open hole at a distal end portion and reference light separated from the light from the light source are synthesized, the imaging apparatus for diagnosis comprising:
    line data generation means for generating line data in a radial direction from a rotary center position of the imaging core based on the interference light data;
    determination means for determining whether or not a foreign substance other than a predetermined liquid enters between the imaging core and an inner surface of the catheter based on distribution of signal strength values in the line data which is generated by the line data generation means; and
    display means for displaying a message which indicates that entrance of the foreign substance is detected in a case where a determination result of the determination means indicates the entrance of the foreign substance.

2. The imaging apparatus for diagnosis according to claim 1, wherein the display means displays a message urging a user to perform priming in which the predetermined liquid fills an inside of the catheter.

3. The imaging apparatus for diagnosis according to claim 1, further comprising:
control means for prohibiting transition to next processing when the determination result of the determination means indicates the entrance of the foreign substance.

4. The imaging apparatus for diagnosis according to claim 1,
wherein the foreign substance which is a determination target of the determination means is an air bubble or blood.

5. A method of controlling an imaging apparatus for diagnosis accommodating an imaging core which has an optical transceiver for transmitting light from a light source toward a vascular tissue and for receiving reflected light from the vascular tissue, and reconstructing a blood vessel image based on interference light data obtained by converting into an electric signal interference light in which measurement light obtained by rotating the imaging core by using a catheter which has an open hole at a distal end portion and reference light separated from the light from the light source are synthesized, the method of controlling an imaging apparatus for diagnosis comprising:
generating line data in a radial direction from a rotary center position of the imaging core based on the interference light data;
determining whether or not a foreign substance other than a predetermined liquid enters between the imaging core and an inner surface of the catheter based on distribution of signal strength values in the generated line data; and
displaying a message which indicates that entrance of the foreign substance is detected in a case where the entrance of the foreign substance is determined.

6. The method of controlling an imaging apparatus for diagnosis according to claim 5, further comprising:
displaying a message instructing a user to perform priming in which the predetermined liquid fills an inside of the catheter.

7. The method of controlling an imaging apparatus for diagnosis according to claim 5, further comprising:
prohibiting transition to next processing when the entrance of the foreign substance is indicated.

8. The method of controlling an imaging apparatus for diagnosis according to claim 5, wherein the foreign substance is an air bubble or blood.

9. A non-transitory computer readable medium containing a computer program having computer readable code embodied to carry out a method of controlling an imaging apparatus for diagnosis accommodating an imaging core which has an optical transceiver for transmitting light from a light source toward a vascular tissue and for receiving reflected light from the vascular tissue, and reconstructing a blood vessel image based on interference light data obtained by converting into an electric signal interference light in which measurement light obtained by rotating the imaging core by using a catheter which has an open hole at a distal end portion and reference light separated from the light from the light source are synthesized, the method of controlling an imaging apparatus for diagnosis comprising:
generating line data in a radial direction from a rotary center position of the imaging core based on the interference light data;
determining whether or not a foreign substance other than a predetermined liquid enters between the imaging core and an inner surface of the catheter based on distribution of signal strength values in the generated line data; and
displaying a message which indicates that entrance of the foreign substance is detected in a case where the entrance of the foreign substance is determined.

10. The non-transitory computer readable medium according to claim 9, further comprising:
displaying a message instructing a user to perform priming in which the predetermined liquid fills an inside of the catheter.

11. The non-transitory computer readable medium according to claim 9, further comprising:
prohibiting transition to next processing when the entrance of the foreign substance is indicated.

12. The non-transitory computer readable medium according to claim 9, wherein the foreign substance is an air bubble or blood.

* * * * *